United States Patent [19]

Vrba et al.

[11] 4,353,257

[45] Oct. 12, 1982

[54] NONDESTRUCTIVE SYSTEM FOR TESTING THE THICKNESS OF BOILER TUBES IN BOILERS

[75] Inventors: Jiri Vrba, Port Coquitlam; Alistair A. Fife, Coquitlam; Max B. Burbank, Maple Ridge; Vaclav Macura, North Vancouver; Randy K. Lomnes, Port Coquitlam, all of Canada

[73] Assignee: Her Majesty the Queen in right of Canada as represented by the Minister of National Defence, Ottawa, Canada

[21] Appl. No.: 222,937

[22] Filed: Jan. 6, 1981

[30] Foreign Application Priority Data

Jan. 11, 1980 [CA] Canada .................................. 343465

[51] Int. Cl.$^3$ ...................... G01B 17/02; G01N 29/04
[52] U.S. Cl. .......................................... 73/623; 73/615; 73/592; 73/598; 364/507; 364/563
[58] Field of Search ....................... 364/506, 507, 563; 73/592, 598, 615, 623, 637, 638

[56] References Cited

U.S. PATENT DOCUMENTS

| | | | |
|---|---|---|---|
| 3,474,664 | 10/1969 | Mitchell et al. | 73/615 |
| 3,929,006 | 12/1975 | Boggs et al. | 73/615 |
| 4,006,359 | 2/1977 | Sullins et al. | 73/623 |
| 4,052,887 | 10/1977 | Sheridan et al. | 73/592 |
| 4,229,796 | 10/1980 | Garrett | 364/506 |
| 4,306,459 | 12/1981 | Johnson et al. | 73/623 |

*Primary Examiner*—Howard A. Birmiel
*Attorney, Agent, or Firm*—William R. Hinds

[57] ABSTRACT

The present invention relates to a system for the nondestructive testing of the thickness of boiler tubes. The system comprises a probe assembly which includes a mounting unit for mounting the assembly in a mud or water drum of a boiler at the location of a boiler tube to be tested. The probe assembly is comprised of an ultrasonic transducer for transmitting and receiving ultrasonic signals. The probe assembly further includes a motor drive connected to the transducer. A control unit is provided which includes a motor control portion connected to the motor drive to selectively position the transducer at a plurality of locations in the boiler tube to be tested. The control unit also includes an ultrasonic drive for producing an ultrasonic pulse for driving said transducer means. A water control is connected to the control unit, a source of water supply, a drain, and the probe assembly. The water control selectively fills the boiler tube in a region of the boiler tube prior to testing and drains the boiler tube after testing. An electronic storage unit is provided, connected to the transducer, via the control unit for storing data relating to wall thicknesses at each of the plurality of locations. An output stage is provided which is connected to the storage unit via the control unit for outputting the data.

16 Claims, 9 Drawing Figures

000
NONDESTRUCTIVE SYSTEM FOR TESTING THE THICKNESS OF BOILER TUBES IN BOILERS

The present invention relates to the nondestructive testing of the thickness of boiler tubes. The system uses ultrasonic techniques to determine the wall thickness of boiler tubes in the location of their connection in the boiler to the mud or water drum. It is at this location within the boiler where corrosion and deterioration of the boiler tubes is highest and therefore, as a safety precaution, it is necessary to periodically inspect the boiler tubes to determine the state of repair of the tubes.

Other ultrasonic systems are not automatic and since a boiler can have many hundreds of boiler tubes, it is an arduous task to manually check all the tubes.

One embodiment of the system according to the present invention can be set to perform the test on a manual, a semi-automatic or an automatic basis. An operator working within the mud drum itself, positions for the acoustic probe assembly within the mud drum at the entrance of a boiler tube to be tested. Once the assembly is in position, the operator presses a button on the assembly and the system is automatically set in motion. The tube is automatically filled with a sufficient quantity of water to ensure good ultrasonic conduction. An ultrasonic transducer is inserted into the boiler tube to a starting position within the boiler tube. From that starting position, the transducer is moved in a helical path to some maximum preselected finished depth. As the ultrasonic transducer is following its helical path, it is momentarily stopped many times per revolution, and at each stop transmits an impulse of energy through the water to the wall of the boiler tube. The transducer subsequently receives an echo from both the inside and outside surfaces of the boiler tube. Since the frequency of the energy impulse and the material from which the boiler tube is made, are known, the time period between the receipt of the echoes from the inside and the outside surfaces of the boiler tube can be translated into a quantity which is representative of the wall thickness of the boiler tube. The system repeats the test several times at each location of the transducer. The results are averaged and compared with limits which are preset into the system. If the averaged value falls within these limits, a valid reading is obtained. The position of the transducer and the thickness of the boiler tube at that position are then stored in a computer memory. When the ultrasonic transducer has finished its helical travel to the finishing depth, it is then automatically withdrawn into the probe assembly. The water is drained from the tube, and the stored position and thickness data are fed to an output unit thereby emptying the computer memory. The output unit can take the form of an X-Y recorder or a strip chart plotter. As a result, a visual indication of the wall thickness with respect to position in the boiler tube is made.

The system is then ready to be placed in position to automatically test the next boiler tube.

In the semi-automatic mode, when the probe assembly is positioned, an initiate scan switch must be activated. The transducer moves to the start position within the tube, automatically performs the scan to the finishing position and then returns to the starting position. A new scan of the tube cannot be started until the memory is cleared. Once the memory has been cleared, the scan can be repeated or the test can be manually terminated, whereby the transducer is moved to its safe position within the probe assembly and the water is drained from the boiler tube.

In the manual mode, the scanning is done from outside the mud drum by an operator located at the main frame of the system. Once the probe assembly is placed in position by the operator working inside the mud drum, he activates a mud drum switch. After the tube has been filled with water and the transducer advanced to the start position, a busy light is switched off on the main frame and a ready light is switched on. If desired, the external operator may limit the length of the scanning path by adjusting the extent of measured tube length control. The transducer is moved in or out of the generator tube by means of an in or out switch. The rate at which the scanner is advanced is controlled by the adjustment of a rate switch which can be set to either single step, slow, medium or fast. The transducer continues to move as long as the in or out switches are depressed for the slow, medium and fast scanning rates. In the single step position, each depression of the in or out switch moves the transducer one step.

When the transducer is moved by means of the in or out switches, the data measured at each stop of the transducer is stored in the memory location corresponding to the given position of the transducer. If the external operator attempts to drive the transducer beyond the allowed limit set by the extent-of-measured-tube-length switch, a tube-extent-exceeded light switches on and the transducer is stopped. The transducer can then be moved only in the opposite direction. The data stored in memory must be manually removed by depressing a memory erase or a memory dump switch. Once the memory is cleared, the memory-not-cleared light switches off and the transducer is retracted to a safe position within the probe assembly.

SUMMARY OF THE INVENTION

It is therefore an object of the present invention to either manually, semi-automatically or automatically determine, using nondestructive testing techniques, the thickness of boiler tubes within a boiler wherein wall thickness data is stored with respect to an exact position on the boiler tube.

In accordance with an aspect of the present invention there is provided a system for the nondestructive testing of the thickness of boiler tubes, comprising: a probe assembly including mounting means for mounting the assembly in a mud or water drum of a boiler at the location of a boiler tube to be tested, said probe assembly comprising ultrasonic transducer means for transmitting and receiving an ultrasonic signal and motor drive means connected to said transducer means; a control means including a motor control portion connected to said motor drive means to selectively position said transducer means at a plurality of locations in said boiler tube to be tested and ultrasonic drive means for producing an ultrasonic pulse for driving said transducer means; water control means connected to said control means, a source of water supply, a drain, and said probe assembly, to selectively fill said boiler tube to be tested in a region of said boiler tube to be tested prior to testing and to drain said boiler tube to be tested after testing; electronic storage means connected to said transducer via said control means for storing data relating to wall thickness at each of said plurality of locations; and output means connected to said storage means via said control means for outputting said data.

DESCRIPTION OF THE DRAWINGS

The present invention will be described in detail hereinbelow by way of example with the aid of the accompanying drawings in which.

DETAILED DESCRIPTION

Figure 1:
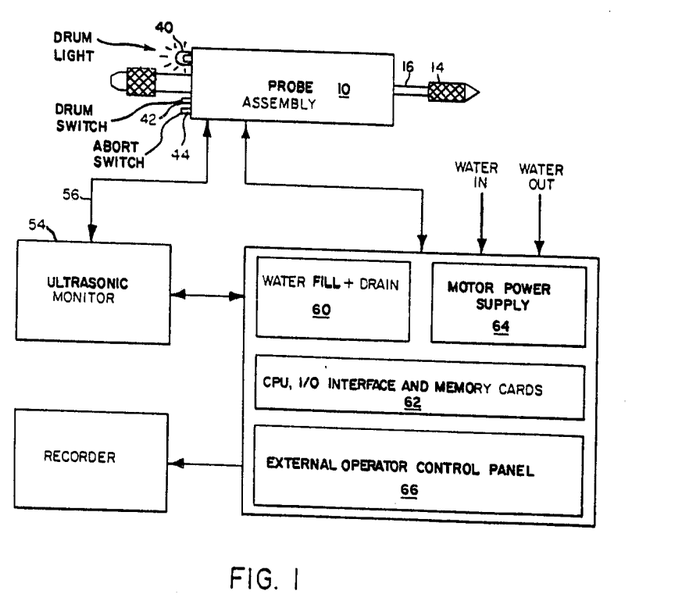
FIG. 1 is a block diagram of a system according to the present invention.
Figure 4:
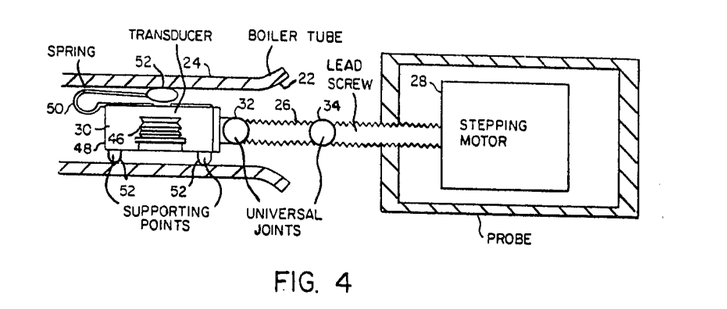
FIG. 4 is a schematic diagram of the probe assembly of the system.
Figure 5:
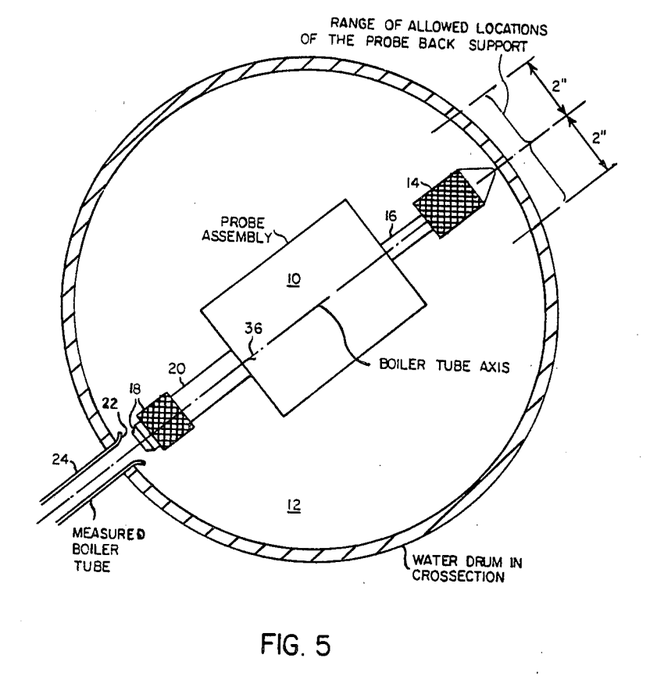
FIG. 5 is a schematic diagram of the probe assembly as located in a mud drum of a boiler to be tested.

A block diagram of the overall system is shown in FIG. 1. The PROBE assembly 10 contains a motor drive, a transducer and a mechanical coupling which joins the transducer to the motor so that rotation of the motor causes the transducer to move in a helical path into and out of a boiler tube to be tested. The assembly 10 is positioned in a mud or water drum 12 (see FIG. 5). Mechanical extension 14 is threaded on shaft 16 and can be extended to the mud drum wall at a position directly opposite the entrance of the boiler tube to be tested. This positions the PROBE assembly for the test. A water-tight seal 18 is threaded onto a hollow shaft 20 and is tightened against the end 22 of the boiler tube 24 to be tested. As can be seen in FIG. 4, the mechanical coupling 26 joining the motor 28 to the transducer 30 contains two universal joints 32 and 34. These joints allow for a smooth movement of the transducer into and out of the boiler tube even when the longitudinal axis of PROBE assembly 10 is slightly misaligned with respect to the longitudinal axis 36 of the boiler tube. With the embodiment shown, a 7 degree misalignment can be tolerated. With the PROBE shown in FIG. 5, this misalignment translates to an acceptable misalignment radius at the point of contact between the mud drum inner wall and the mechanical extension 14 of approximately 2 inches.

The PROBE assembly 10 also includes a water inlet and outlet passage 38 (see FIG. 2) for filling boiler tube 24 with water in the region of the tube to be tested to ensure good transmission of the ultrasonic signal to and from transducer 30. The system fills the tube prior to the test and drains the tube after the test.

Figure 2:
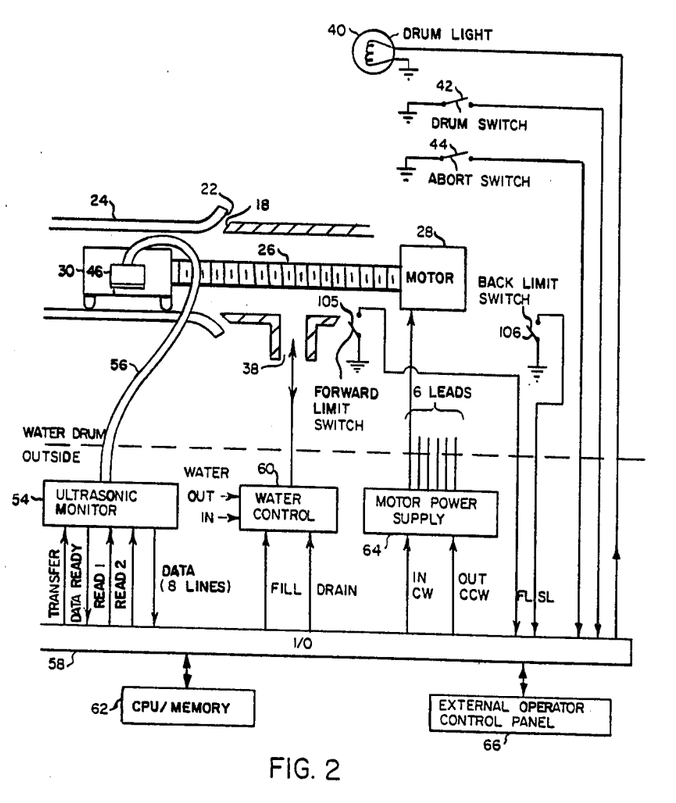
FIG. 2 is a schematic diagram of the system.

PROBE assembly 10 also includes a DRUM light 40, a DRUM switch 42 and an ABORT switch 44 (see FIGS. 1 and 2). If the DRUM light 40 is illuminated a measurement is in progress and the PROBE assembly is not to be moved. The DRUM switch 42 allows the drum operator to initiate a measurement. Activation of the ABORT switch 44 stops the measurement. Upon abort, the system stops all mechanical motion, stops filling the tube with water if activated during the filling phase and initiates 30 seconds of draining.

The PROBE assembly includes transducer 30 (see FIG. 4). The transducer is comprised of an active element 46 mounted very precisely on a carriage 48. The carriage is positioned within the boiler tube 24 by spring 50 and hardened supporting points 52, one of which is located at the end of spring 50. The spring 50 urges the carriage 48 against the inside wall of the boiler tube. This positions the element 46 precisely with respect to the inside wall of the boiler tube. Precise positioning is important since the distance determines the quality of the echo signal being received by the transducer element from both the inside and outside surfaces of the boiler tube wall.

The remainder of the system is located on a main frame outside the mud or water tube (see FIG. 2).

An ultrasonic MONITOR 54 is attached to the transducer element 46 by a coaxial cable 56. The ultrasonic MONITOR 54 generates an ultrasonic signal which drives the transducer 46. In addition, MONITOR 54 receives the ultrasonic echo signals from tranducer 46 and digitalizes them. The digitalized signals are fed to a I/O interface within the MONITOR which is, in turn, connected to I/O INTERFACE 58.

A WATER CONTROL system 60 is also connected to I/O INTERFACE 58. The WATER CONTROL system 60 is connected to the inlet 38 in PROBE assembly 10 by a flexible hose. In addition, a water supply and a drain are connected to WATER CONTROL system 60. The water pressure of the supply can be used to fill the boiler tube 24 or alternatively, a pump could be incorporated into the control system.

A CPU, shown in block CPU/MEMORY 62 controls the operation of the entire system and is connected to I/O INTERFACE 58. The operation of the CPU and the memory will be discussed below with respect to the operation of the entire system.

The transducer must be stationary when the actual test of the boiler tube is being made. As a result, a stepping motor is used to drive the transducer. The stepping motor according to the present embodiment stops at two hundred locations per revolution so that a thickness measurement is made every 1.8 degrees. A MOTOR POWER SUPPLY 64 receives signals from the CPU portion of CPU/MEMORY 62 and controls the movement of the motor 28.

Figure 3:
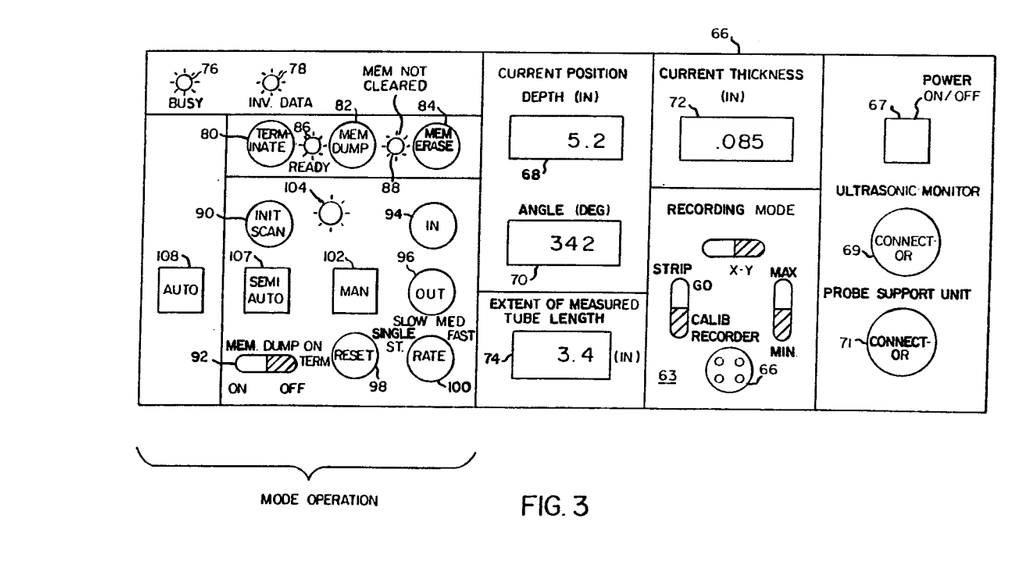
FIG. 3 is a block diagram of the main frame control panel of the system.

The embodiment illustrated has three modes of operation which will be explained with reference to FIG. 3 which shows the external operator's control panel 66.

The right-most portion of control panel 66 includes ON/OFF POWER switch 67 and connectors 69 and 71 for connecting the main frame of the system to the PROBE assembly 10.

The portion 63 of the control panel 66 is the output portion of the system and contains a plug and controls for operating various recording instruments. For example, a strip recorder or an X-Y plotter could be connected to the system via plug 66. Apparatus connected to the system for recording data gathered by the system is of a known type and does not form part of the present invention. The center portion of the control panel includes digital displays. DEPTH display 68 shows the current depth in inches of the measuring position into the boiler tube 24. ANGLE display 70 indicates in degrees the orientation of the measurement. CURRENT THICKNESS display 72 indicates the thickness of the tube 24 at the position shwon in DEPTH and ANGLE displays 68 and 70, respectively. The boiler tube can curve a short distance from its end and, as a result, there is a maximum depth which can be measured into the tube. This maximum depth is determined prior to measurement and is fed into the system by setting EXTENT OF MEASURED TUBE LENGTH switches shown at 74. This maximum depth is constrained either by the travel of the mechanical coupling 26 in PROBE assembly 10 or by curvature of the boiler tube.

The left-most portion of the control panel 66 is used to set the type of mode of operation. The embodiment according to the present invention can either be set on automatic, semi-automatic or manual. The BUSY and INVALID DATA lights 76 and 78, respectively, relate to all three of these modes of operation. TERMINATE switch 80, MEMORY DUMP switch 82 and MEMORY ERASE switch 84 along with READY light 86 and MEMORY NOT CLEARED light 88 apply only to the semi-automatic and automatic modes of operation. INITIATE SCAN switch 90 and MEMORY DUMP ON TERMINATE switch 92 apply only to the semi-automatic mode of operation. IN, OUT, RESET and RATE switches 94, 96, 98 and 100, respectively, apply to the manual mode of operation.

Prior to any measurement, the system must be calibrated. The correlation between the separation of the ultrasonic echoes and the tube thickness of the steel tube can be determined when the DRUM light 40 is off and the system is awaiting the activation of the DRUM switch. To calibrate the system, an auxilliary transducer is connected to ultrasonic MONITOR 54 and inserted in a section of tube of known thickness. The frequency of the ultrasonic oscillator is then adjusted so that the thickness displayed at CURRENT THICKNESS display 72 (see FIG. 3) equals the known thickness of the tube.

The transducer 30 is housed in the PROBE assembly 10 in what is known as a 'safe' position. However, the transducer does not begin measuring the wall thickness of the boiler tube from this safe position. Prior to measurement, motor 28 drives the transducer to a start position located within the neck of the boiler tube. The start position is programmed into the system when the DRUM light 40 is off and the CPU portion of CPU/MEMORY 62 is awaiting activation of the DRUM switch. The required new distance between the starting position and the safe position is dialed on the EXTENT OF MEASURED TUBE LENGTH switch 74 and is entered into the memory by pressing the RESET switch 98. The newly defined start position remains programmed into the system until the power switch is turned off. When the system power is switched on the distance between the starting position and the safe position is automatically set to be equal to 1.4 inches and the procedure set out above must be followed if some other start position is desired. For this setting the transducer in the start position just clears the gap between the PROBE assembly and the generator tube.

System Operation

If the operator selects the manual mode by depressing MANUAL switch 102, the sequence is stopped after the initial preparation actions, i.e. water fill and advance to start position, take place. The BUSY light 76 is switched off and the READY light 86 is switched on. The CPU portion of CPU/MEMORY 62 awaits the action of the external operator. If desired, the operator may limit the length of the scanning path by adjusting the extent of measured tube length in the manner mentioned above. To move the transducer in or out of the boiler tube, the operator presses the IN or OUT switch 94 or 96, respectively. The rate at which the transducer is advanced is controlled by the adjustment of RATE switch 100. The advancement of the transducer can be controlled to single step, slow, medium or fast. The transducer continues to move as long as the IN or OUT switches are depressed in the slow, medium and fast rate settings. In the single step mode, each depression of the IN or OUT switch moves the transducer only one step. The switches have to be released and pressed again if another step is required.

When the transducer is moved by means of the IN or OUT switches, the data measured at each motor stop is stored in the memory location corresponding to the given position of the transducer in the memory portion of CPU/MEMORY 62. If the transducer position is scanned more than once, as for example, by repetitive pressing of the IN and OUT switches, the latest thickness measurement is recorded in memory. If the operator attempts to drive the transducer beyond the allowed limit, FORWARD LIMIT switch 105 is activated (see FIG. 2) and the TUBE EXTENT EXCEEDED light 104 is illuminated and the transducer is halted. The transducer can now only be moved in the opposite direction. In addition, the TUBE EXTENT EXCEEDED light 104 is switched on if the OUT switch is depressed and the transducer has moved all the way back to the safe position. The BACK LIMIT switch 106 (see FIG. 2) is activated, and no further out motion of the transducer is possible. TUBE EXTENT EXCEEDED light 104 is illuminated if the IN switch is depressed and the transducer depth in the tube has reached the depth preset on the EXTENT OF MEASURED TUBE LENGTH switch 74. The light is also illuminated if the IN switch is depressed and the transducer has reached the full length of its travel as constrained by the mechanical coupling 26. This only occurs if the measured tube length switch has been adjusted to depths which are greater than lengths achievable by the mechanical coupling 26.

Regardless of its position, the transducer can always be quickly reset to its starting position by activating the RESET switch 98. At any time during the scan sequence the data accumulated in memory can be erased by the MEMORY ERASE switch 84 or plotted by activation of the MEMORY DUMP switch 82.

The measurement of a given boiler tube can be terminated by pressing the TERMINATE switch 80. The READY light 86 switches off and the BUSY light 76 switches on. If there is unrecorded data in memory, the MEMORY NOT CLEARED light 88 switches on and the system waits until the memory is cleared. This can be done either by depressing the MEMORY ERASE switch 84 or the MEMORY DUMP switch 82. This provision has been built into the program of the CPU portion of CPU/MEMORY 62 to prevent the unintentional loss of memory data. Once the memory is cleared, the MEMORY NOT CLEARED light 88 switches off and the transducer is retracted to its safe position. At this point, the sequencing of the thickness data is interrogated and the minimum and maximum thicknesses are established. This procedure will be described below. The minimum thickness is displayed on the ANGLE display 70 and the maximum thickness is displayed on the DEPTH display 68. In both cases, the units are in mils. Next, the water is drained from the tube, the DRUM light 40 (see FIGS. 1 and 2) is switched off, the the CPU portion of CPU/MEMORY 62 awaits initiation of the DRUM switch corresponding to the measurement of a new boiler tube.

A semi-automatic mode can be selected by depressing SEMI-AUTO switch 107. When the semi-automatic mode is selected by the operator and after the preparation procedure is complete, the BUSY light 76 switches off and the READY light 86 switches on. At this stage, the system awaits further action by the operator. The boiler tube can now be scanned by depressing the INITIATE SCAN switch 90. Upon activation of the INITIATE SCAN switch, the READY light 86 switches off, the BUSY light 76 switches on, and the transducer begins an automatic scan of the boiler tube. The scanning and the data recording begins at the starting position and ends at the forward limit position. The transducer is then automatically reset to the starting position and the MEMORY NOT CLEARED light 88 switches on. The BUSY light 76 switches off and the READY light 86 switches on. A new scan of the tube cannot be started until the memory is cleared to prevent unintentional loss of data. The memory can be cleared either by the MEMORY ERASE switch 84 or by the MEMORY DUMP switch 82. After the memory is cleared, the MEMORY NOT CLEARED light 88 switches off and the tube scanning can be repeated.

When the READY light 86 is on, the measurement can be terminated by the TERMINATE switch 80. If the memory is clear, the termination begins. However, if the memory is not clear, the MEMORY NOT CLEARED light 88 switches on and the system reads the state of the MEMORY DUMP ON TERMINATE switch 92. If it is "on" the data recording proceeds automatically. However, if MEMORY DUMP ON TERMINATE switch 92 is "off" the system waits until the memory is cleared. The memory can be cleared, by switching on the MEMORY DUMP ON TERMINATE switch 92 or by activating the MEMORY ERASE switch 84 or the MEMORY DUMP switch 82. Once the memory is clear, termination can begin.

In terminating, the transducer is retracted back to its safe position within the PROBE assembly 10 and the minimum and maximum thicknesses are calculated and displayed on the DEPTH and ANGLE displays 68 and 70, respectively. The water is drained from the boiler tube and the DRUM light is switched off. The system now awaits the initiation of a new measurement.

Automatic operation of the system can be initiated by pressing AUTO switch 108. In the automatic mode, the system goes through the initializing procedure and automatically advances to the scanning sequence. The transducer scans the tube from the starting position to the forward limit position with corresponding thickness data being stored in memory. The transducer is retracted to its starting position and the data recording is initiated. When the recording is complete, the transducer is retracted into the safe position within the PROBE assembly 10 and the maximum and minimum thicknesses are calculated and displayed, as before, on the DEPTH and ANGLE displays 68 and 70, respectively. The water is drained and the DRUM light is switched off and the system awaits the initiation of a new measurement.

As mentioned above, the maximum and minimum thicknesses of the tube being measured are displayed. To establish these maximum and minimum points, the memory is examined and the absolute minimum thickness of the five largest thicknesses are located. The five largest thickness points are averaged in arriving at the maximum value. However, not all measured data is examined. This is the case, since the starting position could be located at the joint between the boiler tube and the mud drum and so the initial data points are often erroneous. For this reason the starting address for the data interrogation is set outside the joint between the mud drum and the boiler tube at 1.4 inches past the starting position.

Figure 6:
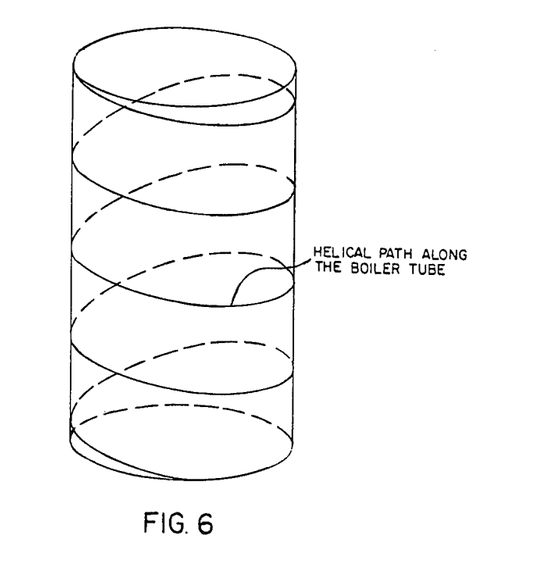
FIG. 6 (appearing on the same sheet of drawings as FIG. 4) is a graphical representation showing the path of the transducer within a boiler tube being tested.

As was mentioned above, the motor 28 stops transducer 30 at two hundred locations per revolution along a helical path shown in FIG. 6. In other words, the transducer stops at every 1.8 degrees of angular rotation. However, the system automatically, under the supervision of the CPU/MEMORY 62, groups 10 such stops together and ultimately only memorizes data for every 18 degrees of angular rotation of the transducer. As a result, twenty thickness measurements spaced 18 degrees apart are accumulated during one rotation of the transducer. The mechanical coupling 26 is designed so that one rotation of the motor 28 advances the transducer 0.1 inch into or out of the boiler tube 24. As a result, one inch of tube length is scanned two hundred times.

Figure 7:
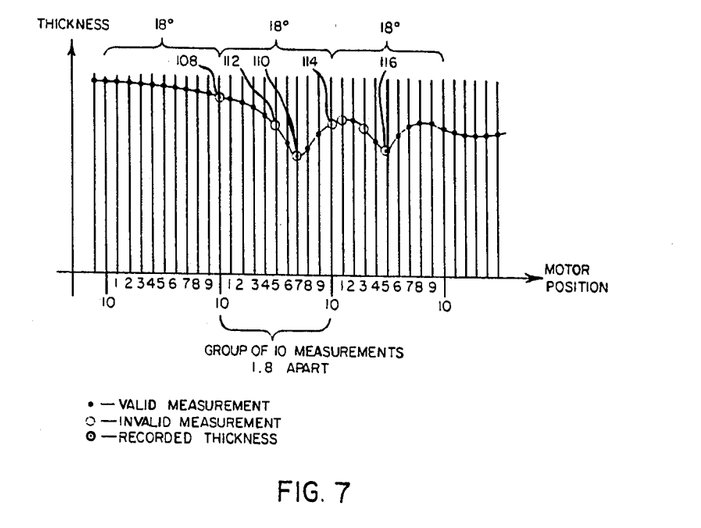
FIG. 7 is a plot of wall thickness of a boiler tube with respect to the position of the transducer.

The condensation of data measured during 10 successive motor steps is performed, as was mentioned above by CPU/MEMORY 62. Invalid measurements are eliminated and for the remaining measurements the minimum value is selected and recorded. The process is repeated each 10 motor stops. The number of points of valid data within each group of 10 motor stops is counted and when the number is less than a predetermined constant limit, the ten measurements are defined as invalid and a zero is recorded in the corresponding memory space. This limit is preselected to equal 1, however the limit can be changed. FIG. 7 illustrates three such groups of ten measurements. Point 108 in the first group of ten measurements is the minimum thickness point and would be the value recorded in the appropriate memory space. Point 110 is the minimum value recorded in the next group of 10 motor stops. However, in this instance, point 112 and point 114 are defined as invalid measurement points. However, since only 2 out of 10 points are invalid, the predetermined limit of 1 has not been met and so the second group of measurement points is valid. Similarly, point 116 is determined to be the minimum thickness point in the third group of 10 successive motor stops.

At each motor stop, eight wall thickness measurements are obtained and averaged. The average number is the measured thickness and is stored in memory. If for some reason, either the back surface echo or a front surface echo is not received, the thickness of the boiler tube at that motor stop cannot be measured. If this happens, the measurement at a given motor stop is repeated until eight valid thickness measurements are accumulated. However, in order that the system not stall at a particularly bad motor stop, if no acceptable data is received within twenty-five measurements, a zero is inserted in the appropriate memory space and that motor stop is defined as being an invalid measurement.

CPU/MEMORY 62 has been programmed so that if the system is operating in the automatic or semi-automatic modes, and if 0.5 inch of tube length exhibits continual invalid measurements in sequence, the mode of operation is automatically switched to manual. This occurrence of continuous invalid data is very likely due to the improper adjustment of the ultrasonic MONITOR 54.

Figure 8:
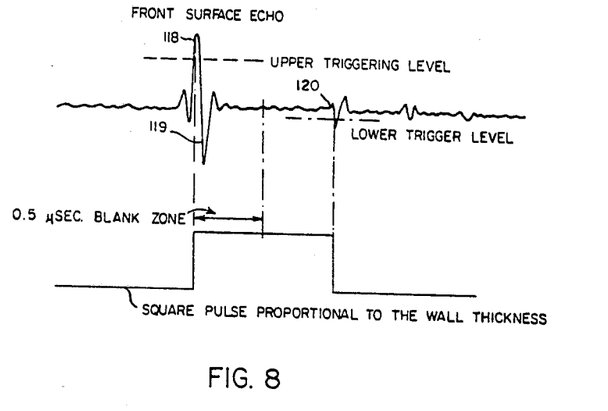
FIG. 8 is a diagram of an ultrasonic signal received by the transducer according to the system.

FIG. 8 of the drawings shows how a square pulse proportional to the wall thickness of the boiler tube being measured is derived from the echo pulses received by transducer 30. Transducer 30 transmits a drive pulse not shown in FIG. 8. This drive pulse reflects from the front surface of the boiler tube and is shown in FIG. 8 as a strong positive peak 118. The front surface echo pulse characteristically is immediately followed by a strong negative going signal 119. Some considerable time length later echo pulse 120 is received by transducer 30. This echo pulse represents an echo reflected from the outer surface of the boiler tube being tested. It characteristically exhibits a fairly strong negative going signal. In order that the ultrasonic MONITOR 54 is not triggered by the false negative-going pulse 119, ultrasonic MONITOR 54 is automatically blanked for a time period immediately after receipt of the strong positive going front surface echo pulse 118. Typically, this blanking period is in the neighbourhood of 0.5 microsecond. During this time period, due to the physical location of the transducer with respect to the front surface of the boiler tube being tested, no valid pulses would be received and, as a result, there is no possibility that the blanking time period would inhibit the valid receipt of the echo signal from the outer surface of the boiler tube being tested.

Echo signal 118 activates electronic circuitry, as for example a Schmitt trigger, within ultrasonic MONITOR 54. Echo signal 120 shuts off the Schmitt trigger. As a result, a digital square pulse is produced having an "on" time which is proportional to the wall thickness of the boiler tube being measured. Ultrasonic MONITOR 54 digitalizes the duration of the square pulse thereby producing a digital value which is proportional to wall thickness. It is this digital signal which is stored in CPU/MEMORY 62 and which is manipulated by the CPU portion to produce the data described above.

Figure 9:
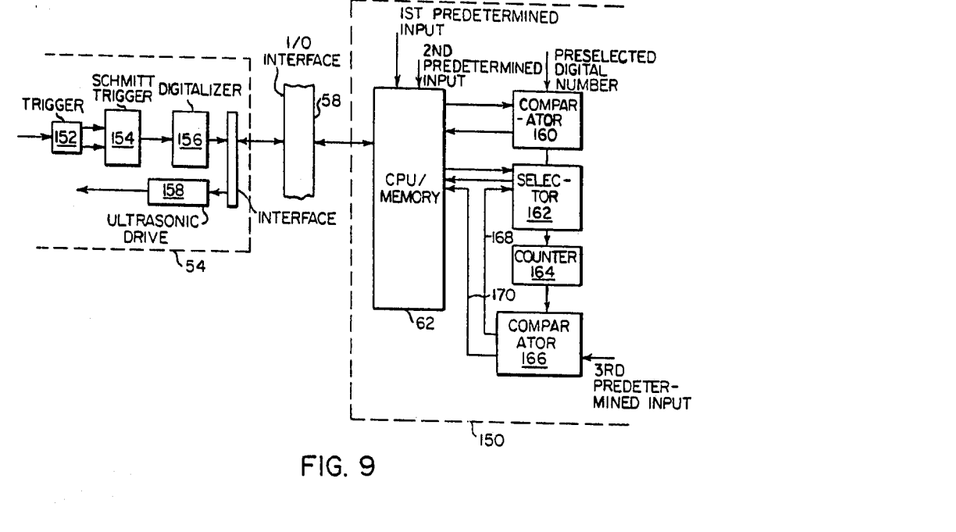
FIG. 9 is a block diagram of a portion of the block diagram shown in FIG. 1.

One possible operation of the system is shown in FIG. 9 which shows a portion of the ultrasonic MONITOR 54, I/O INTERRFACE 58 and a CONTROL circuit 150 part of which is formed by CPU/MEMORY 62.

As was mentioned above with respect to FIG. 8, incoming data from the transducer 30 is fed to a TRIGGER 152 within ultrasonic MONITOR 54. The positive and negative going pulses control the operation of a Schmitt trigger 154. The Schmitt trigger 154 produces a positive going pulse, the duration of which is proportional to the wall thickness of boiler tube 24. This pulse is digitalized with respect to its duration by DIGITALIZER 156 and the resulting digital number is stored in memory via I/O INTERFACE 58 and CPU/MEMORY 62.

The CPU of CPU/MEMORY 62 repeats the test a predetermined number of times by activating ultrasonic DRIVE 158. The results of these tests are fed to COMPARATOR 160 and compared with a preselected digital number to test the validity of each result. If the first predetermined number of results are not all valid, COMPARATOR 160 signals the CPU of CPU/MEMORY 62 to continue making tests at that testing stop by activating ultrasonic DRIVE 158. This process carries on until either the first predetermined number of valid tests are obtained or a second predetermined number of tests have been carried out. If the first predetermined number of valid tests have been obtained the CPU of CPU/MEMORY 62 averages the results and stores the resulting digital number in an associated memory position within the memory portion of CPU/MEMORY 62. If the first predetermined number of valid test results are not obtained by the time the second predetermined number of repeated tests have been made, a zero is stored in memory representing an invalid test result at the testing stop position. When all the points along the helical path shown in FIG. 6 have been tested, as was mentioned above, several adjacent testing stops are grouped together. This is performed by SELECTOR 162. The number of valid test points within a group are counted by COUNTER 164 and the count is fed to COMPARATOR 166. COMPARATOR 166 compares the count with a third predetermined input to determine if the number of valid tests within a group are sufficient to determine a valid thickness measurement for the group. If COMPARATOR 166 determines that a great enough number of valid tests fall within a group, a signal is sent to SELECTOR 162 via line 168, and SELECTOR 162 chooses the smallest test result within the group. This result is stored in the memory of CPU/MEMORY 62 as the thickness measurement for the group in question. If on the other hand, an insufficient number of valid test points are received within a group, COMPARATOR 166 signals the CPU of CPU/MEMORY 62 via line 170 to place a zero in memory for that group position.

As a result, if a given length of boiler tube 24 was measured in n locations, and m measurements were grouped together the final outputted data would include n/m thickness measurements at n/m positions along that length of boiler tube.

It should be understood that the electronic circuitry and components contained in ultrasonic MONITOR 54, CPU/MEMORY 62, I/O INTERFACE 58 and MOTOR POWER SUPPLY 64 are known. The CPU portion of CPU/MEMORY 62 operates via a known series of pre-programmed subroutines which do not form part of the present invention.

We claim:
1. A system for the nondestructive testing of the thickness of boiler tubes, comprising:
(a) a probe assembly including mounting means for mounting the assembly in a mud or water drum of a boiler at the location of a boiler tube to be tested, said probe assembly comprising ultrasonic transducer means for transmitting and receiving an ultrasonic signal and motor drive means connected to said transducer means;
(b) a control means including a motor control portion connected to said motor drive means to selectively position said transducer means at a plurality of locations in said boiler tube to be tested and ultrasonic drive means for producing an ultrasonic pulse for driving said transducer means;
(c) water control means connected to said control means, a source of water supply, a drain, and said probe assembly, to selectively fill said boiler tube to be tested in a region of said boiler tube to be tested prior to testing and to drain said boiler tube to be tested after testing;
(d) electronic storage means connected to said transducer via said control means for storing data relating to wall thickness at each of said plurality of locations; and
(e) output means connected to said storage means via said control means for outputting said data.

2. The system according to claim 1 wherein said control means further includes an echo receiving circuit for receiving first and second ultrasonic echo signals received by said transducer means from the inner and outer surfaces of said boiler tubes being tested, respectively.

3. The system according to claim 2 wherein said echo receiving circuit controls a logic circuit to produce a positive going pulse, said pulse having a leading and a trailing edge wherein said echo receiving circuit triggers said logic circuit to produce said leading edge upon receipt of said first ultrasonic echo signal and wherein said echo receiving circuit resets said logic circuit to produce said trailing edge upon receipt of said second ultrasonic echo signal so that the duration of said positive going pulse is proportional to the time duration between receipt of said first and second ultrasonic echo signals.

4. The system according to claim 3 wherein said control means further includes blanking means wherein, upon receipt of said first ultrasonic signal said echo receiving circuit is made insensitive to receipt of any ultrasonic signal for a predetermined time period which time period is less than the duration between receipt of said first and second ultrasonic echo signals.

5. The system according to claim 4 wherein said predetermined time period is about 0.5 microsecond.

6. The system according to claim 3 wherein said logic circuit includes a Schmitt trigger.

7. The system according to claim 4 further including a digitalizing circuit which produces a digital number which is directly proportional to said duration of said positive going pulse.

8. The system according to claim 7 wherein the control circuit includes a central processing unit (CPU) which produces a plurality of initiate signals which control said water control means to fill said boiler tube to be tested and which control said motor control portion to energize said motor drive means to move said transducer means from a safe position within said probe assembly to a start position within said boiler tube to be tested.

9. The system according to claim 8 wherein said CPU produces a plurality of terminate signals which control said motor control portion to energize said motor drive means to move said transducer means from said start position to said safe position, and which control said water control means to drain said boiler tube being tested after said test is complete.

10. The system according to claim 9 wherein said motor drive means includes a stepping motor which is controllable by said motor control portion to stop a plurality of times per revolution, and a mechanical linkage joining said transducer to said motor so that said transducer describes a helical path within said boiler tube being tested when driven by said stepping motor, said transducer thereby making n testing stops along said helical path, where n is a positive integer.

11. The system according to claim 10 wherein said mechanical linkage includes two universal joints to provide the smooth movement of said transducer along said helical path when there is slight misalignment between the longitudinal axis of said boiler tube and the longitudinal axis of said probe assembly.

12. The system according to claim 10 wherein said CPU produces signals to control said motor control portion to drive said transducer from said starting position along said helical path to a predetermined finished position, wherein said CPU produces signals to activate said ultrasonic drive means at each of said n testing stops to thereby generate said digital number for each of said n testing stops, each said digital number being stored in said storage means in a memory position which corresponds with its associated testing stop.

13. The system according to claim 12 wherein said control means further includes a comparator means and wherein said CPU, at each of said n testing stops, repeats said signals to activate said ultrasonic drive means in the following sequence:

(f) said CPU repeats said signals a first predetermined number of times to produce a first predetermined number of digital numbers;

(g) said comparator means compares each of said first predetermined number of digital numbers with a preselected limiting digital number to determine which of said first predetermined number of digital numbers are valid, said comparator means producing a signal which causes said CPU to produce additional repeat signals for each of said first predetermined number of digital numbers that are invalid, said comparator means continuing to repeat said signals until either said first number of predetermined digital numbers are obtained or a second predetermined number of total repeat signals are produced; and (h) said CPU then either automatically averages said first predetermined number of digital numbers to produce a final valid digital number if said first predetermined number of digital numbers have been obtained or said CPU produces a digital signal representing an invalid digital number if said first predetermined number of digital numbers have not been obtained, said storage means then storing either said final valid digital number or said digital signal representing an invalid digital number in a memory position which corresponds with its associated testing stop.

14. The system according to claim 13, wherein said first predetermined number is eight and wherein said second predetermined number is twenty-five.

15. The system according to claim 14, wherein said control means includes a selection means, a counting means and a second comparator means, wherein said selection means group together the digital numbers associated with m adjacent testing stops, where $1 > m > n$, thereby forming a group of m digital numbers, said counting means counting the number of final valid digital numbers in said group of m digital numbers and producing a digital count signal representative of the number of final valid numbers in said group of m digital numbers, said comparator means comparing said digital count signal with a predetermined digital count signal, said comparator means producing a first compared count signal, fed to said selection means, if said digital count signal is greater than said predetermined count signal to cause said selection means to select the smallest final valid digital number of said group of m digital numbers, said smallest final valid digital number being stored in a memory position associated with said group of m adjacent testing stops, or a second compared count signal if said digital count signal is less than said predetermined count signal, said second compared count signal being fed to said CPU to cause said CPU to store an invalid group number in said memory position associated with said group of m adjacent testing stops, said storage means finally storing n/m final digital numbers in n/m memory positions associated with n/m testing stops along said helical path.

16. The systems according to claim 15 wherein said data outputted by said output means corresponds to said n/m final digital numbers and said n/m testing stops along said helical path.

* * * * *